United States Patent [19]
Jefferies

[11] Patent Number: 5,904,718
[45] Date of Patent: May 18, 1999

[54] DELAYED DRUG DELIVERY SYSTEM

[75] Inventor: Steven R. Jefferies, Milford, Del.

[73] Assignee: Biocoll Laboratories, Inc., Seattle, Wash.

[21] Appl. No.: 08/872,210

[22] Filed: Jun. 9, 1997

Related U.S. Application Data

[60] Continuation-in-part of application No. 08/470,368, Jun. 6, 1995, abandoned, which is a division of application No. 08/422,745, Apr. 14, 1995, which is a continuation of application No. 08/057,951, Jan. 29, 1993, abandoned, which is a continuation of application No. 07/892,646, Jun. 2, 1992, abandoned, which is a continuation of application No. 07/718,914, Jun. 24, 1991, abandoned, which is a continuation of application No. 07/119,916, Nov. 13, 1987, abandoned, which is a continuation-in-part of application No. 07/080,145, Jun. 30, 1987, abandoned, which is a continuation of application No. 06/844,886, Mar. 27, 1986, abandoned.

[51] Int. Cl.⁶ ........................................... A61F 2/28
[52] U.S. Cl. ................... 623/16; 623/11; 623/66; 128/898; 606/76
[58] Field of Search .................... 623/11, 16, 66; 606/76, 77; 128/898

[56] References Cited

U.S. PATENT DOCUMENTS

| | | |
|---|---|---|
| 2,516,438 | 7/1950 | Wheeler . |
| 3,767,437 | 10/1973 | Cruz, Jr. . |
| 4,172,128 | 10/1979 | Thiele et al. . |
| 4,193,813 | 3/1980 | Chvapil . |
| 4,209,434 | 6/1980 | Wilson et al. . |
| 4,291,013 | 9/1981 | Wahlig et al. ............................ 623/16 |
| 4,294,753 | 10/1981 | Urist . |
| 4,394,370 | 7/1983 | Jefferies ................................. 424/15 |
| 4,430,760 | 2/1984 | Smestad . |
| 4,434,094 | 2/1984 | Seyedin et al. . |
| 4,440,750 | 4/1984 | Glowacki et al. . |
| 4,455,256 | 6/1984 | Urist ......................................... 623/16 |
| 4,472,840 | 9/1984 | Jefferies . |
| 4,485,097 | 11/1984 | Bell . |
| 4,563,350 | 1/1986 | Nathan et al. . |
| 4,563,489 | 1/1986 | Urist . |
| 4,596,574 | 6/1986 | Urist . |
| 4,619,989 | 10/1986 | Urist . |
| 4,620,327 | 11/1986 | Caplan et al. . |
| 4,623,553 | 11/1986 | Ries et al. . |
| 4,627,982 | 12/1986 | Seyedin et al. . |
| 4,642,120 | 2/1987 | Nevo et al. . |
| 4,678,470 | 7/1987 | Nashef et al. ............................ 623/16 |
| 4,681,763 | 7/1987 | Nathanson et al. . |
| 4,703,108 | 10/1987 | Silver et al. ............................ 530/356 |
| 4,718,910 | 1/1988 | Draenert . |
| 4,743,259 | 5/1988 | Bolander et al. . |
| 4,789,732 | 12/1988 | Urist . |
| 4,795,467 | 1/1989 | Piez et al. ................................. 623/16 |
| 4,861,714 | 8/1989 | Denn, Jr. et al. . |
| 4,975,526 | 12/1990 | Kuberasampath et al. . |
| 5,001,169 | 3/1991 | Nathan et al. . |
| 5,162,114 | 11/1992 | Kuberasampath et al. . |

FOREIGN PATENT DOCUMENTS

WO 89/04646   6/1989   WIPO .

OTHER PUBLICATIONS

F.L. Bye, M.E. Krause, J.A. Regezi, R.G. Caffesse, Histologic Evaluation of Periodontal Implants in a Biologically "Closed" Model, Journal of Periodontology, Feb. 1987.

Donath et al., A Histologic Evaluation of a Mandibular Cross Section One Year After Augmentation with Hydroxyapatite Particles, *Oral Surgery, Oral Medicine, Oral Pathology*, vol. 63, No. 6, pp. 651–655, 1987.

Mellonig, Freeze–Dried Bone Allografts in Periodontal Reconstructive Surgery, from *The Dental Clinics of North America: Reconstructive Periodontics* vol. 35(3):505–520, 1991.

Yamazaki et al., Experimental Study on the Osteoindustion Ability of Calcium Phosphate Biomaterials with Added Bone Morphogenetic Protein, *Transactions of the Society for Biomaterials*, p. 111, 1986.

*Primary Examiner*—Paul B. Prebilic
*Attorney, Agent, or Firm*—Lyon & Lyon LLP

[57] ABSTRACT

A process and product comprising collagen and demineralized bone particles. The product may contain a maximum of 20% by weight inorganic materials. The product may densified by compression. Additional osteogenic factors, mitogens, drugs or antibiotics may be incorporated therein. Inorganic materials may be bound to the organic matrix via precoating with a calcium or hydroxyapatite binding protein, peptide or amino acid. The materials also display long lasting drug release characteristics.

11 Claims, No Drawings

DELAYED DRUG DELIVERY SYSTEM

This application is a continuation of Ser. No. 08/470,368 filed Jun. 6, 1995 and now abandoned which is a division of Ser. No. 08/422,745 filed Apr. 14, 1995 which is a continuation of Ser. No. 08/057,951 filed Jan. 29, 1993 and now abandoned which is a continuation of Ser. No. 07/892,646 filed Jun. 2,1992 and now abandoned which is a continuation of Ser. No. 07/718,914 filed Jun. 24, 1991 and now abandoned which is a continuation of Ser. No. 07/119,916 filed Nov. 13, 1987 and now abandoned which is a continuation-in-part of Ser. No. 07/080,145 filed Jun. 30, 1987 and now abandoned which is a continuation of Ser. No. 06/844,886 filed Mar. 27, 1986 and now abandoned.

TECHNICAL FIELD

The present invention relates to bone repair materials with improved cohesive and physical strength for use in stress-bearing defects or where the ability to produce and maintain the specific shape of an implant is important. The principle of creating a stable interface and conjugate between a protein-based particle and an organic matrix is also applicable to drug delivery materials and devices.

BACKGROUND ART

The repair of osseous defects involves either non-resorbable or resorbable prosthetic structures. The resorbable structures or materials either support the ingrowth of adjacent bone and soft tissue or actively induce the formation of new bone. This active formation of new bone, termed osteoinduction, occurs only in the presence of demineralized bone matrix or in the presence of protein extracts from such matrix, or a combination of both materials. Particles or powders produced from demineralized bone matrix possess greater osteogenic potential per unit weight due to their increased surface area, than blocks or whole segments of demineralized bone.

Other method of repairing damaged or missing osseous tissue or bone have also been explored. Replacement or support with nonresorbable materials, such as biocompatible metals, ceramics, or composite metal-ceramic materials, offers one method of clinical treatment. Some of these materials, such as metal grade titanium, can promote osteocoinduction at their surface, thus leading to a stable, continuous interface with bone. Caffessee et al *Journal of Periodontology*, Feb. 1987 utilizing a "window" implantation technique, established that nonabsorbable ceramics, such as hydroxyapatite, fail to stimulate tissue, even when placed in osseous defects. Resorbable ceramics, such as tricalcium phosphate, display better conduction of mineralized tissue into the resorbing graft material when placed in osseous defects. Unlike demineralized bone matrix, tricalcium phosphate or hydroxyapatite fail to stimulate induction of new bone when placed in non-osseous tissue. The addition of tricalcium phosphate or hydroxyapatite to demineralized bone matrix or to the extracted bone-inducing proteins actually inhibits the osteogenetic potential of these established osteoinductive compositions (see Yamazaki et al. Experimental Study On the Osteoindustion Ability of Calcium Phosphate Biomaterials with added bone Morphogenetic Protein *Transations of the Society For Biomaterials* pg 111, 1986.

Aside from the documented inability of hydroxyapatite and tricalcium phosphate ceramic materials to independently induce osteogenesis, recent clinical findings indicate that osteointegration of inorganic particles is highly dependent on the ability of those particles to remain fixed in a definite position, preferably near a bony interface. Hence, the immobility of the particles is a prerequisite for involvement with new bone formation (See Donath, et. al., A Histologic Evaluation of a Mandibular Cross Section One Year After Augmentation with Hydroxyapatite Particles *Oral Surgery, Oral Medicine, Oral Pathology* vol 63 No. 6 pp. 651–655, 1987.

Nevertheless, numerous compositions have been derived to create clinically useful bone replacement materials. Cruz U.S. Pat. No. 3,767,437 describes artificial ivory or bone-like structures which are formed from a complex partial salt of collagen with a metal hydroxide and an ionizable acid, such as phosphoric acid. With regard to the metal hydroxide, this composition stresses the use of a polyvalent metal cation in the metal hydroxide, such as calcium hydroxide. Calcium phosphate may be added to the complex collagen salt. Cruz also recites the addition of fibers and ions to increase hardness and structural strength, but does not document or make claims with regard to these specific improvements. Cruz does not mention or claim these compositions to be osteoinductive or osteoconductive, nor does he mention their behavior in-vivo.

Thiele, et al., in U.S. Pat. No. 4,172,128, recites a process of degrading and regenerating bone and tooth material and products. This process involves first demineralizing bone or dentin, converting the demineralized material into a mucopolysaccharide-free colloidal solution by extraction with sodium hydroxide adding to the resultant solution a physiologically inert foreign mucopolysaccharide, gelling the solution, and then remineralizing the resulting gel. Thiele et al indicate this material to be biocompatible and totally resorbable, thus replaced by body tissue as determined by histologic analysis the gel material produced by this process is reported to completely replace destroyed bone sections created in experimental animals. The patentees do not indicate any ability by the material to induce new bone. The ultimate fate of these materials in-vivo, or their ability to stimulate the formation of new bone in non-osseous implant sites is not described. The patentees do not describe or quantify the strength properties of these material. Nevertheless, since they are described as gels, one can assume their strength to be low.

Urist In U.S. Pat. No. 4,294,753, describes a process of extracting and solubilizing a Bone Morphogenetic Protein (BMP). This is a glycoprotein complex which induces the formation of endochrondral bone in osseous and non-osseous sites. This partially purified glycoprotein, which is derived from demineralized bone matrix by extraction, is lyophilized in the form of a powder. Urist describes the actual delivery of BMP in in-vivo testing via direct implantation of the powder, implantation of the powder contained within a diffusion chamber, or coprecipitation of the BMP with calcium phosphate. While Urist describes the induction of new bone after the implantation of one of these forms of BMP in either osseous or non-osseous sites, Urist fails to address the intrinsic physical strength properties of any of these delivery forms. Lyophilized powders and calcium phosphate precipitates, however, possess little if any, physical strength. Furthermore, more recent investigators (see aforementioned Yamazasaki, et al) indicate that calcium phosphate ceramics, such as tricalcium phosphate and hydroxyapatite, when present in high concentrations relative to the BMP present, may actually inhibit the osteogenic action of the BMP.

Jefferies in U.S. Pat. Nos. 4,394,370 and 4,472,840 describes bone graft materials composed of collagen and demineralized bone matrix, collagen and extracted Bone Morphogenetic Proteins (BMP). Also described is a combination collagen, demineralized bone matrix, plus extracted bone morphogenetic proteins. Jefferies describes an anhydrous lyophilized sponge conjugate made from these compositions which when implanted in osseous and non-osseous sites, is able to induce the formation of new bone. The physical strength of these sponges is not specified in the disclosure, however, reports of the compressive strength of other collagen sponges indicates these materials to be very weak and easily compressible (much less then 1 kiligram load needed to affect significant physical strain in compression or tension).

Smestad in U.S. Pat. No. 4,430,760 assigned to Collagen Corporation, describes a nonstress-bearing implantable bone prosthesis consisting of demineralized bone or dentin placed within a collagen tube or container. As the patentee indicates, this bone prosthesis can not be used in stress-bearing locations clinically.

Glowacki et al., in U.S. Pat. No. 4,440,7550 apparently assigned to Collagen Corporation and Harvard University describe plastic dispersions of aqueous collagen mixed with demineralized bone particles for use in inducing bone in osseous defects. This graft material, as described exists in a gel state and possesses little physical strength of its own. Its use, therefore, must be restricted to defects which can maintain sufficient form and strength throughout the healing process. Furthermore, with time, the demineralized bone particle suspended within the aqueous collagen sol-gel begin to settle under gravitational forces, thus producing an non-homogeneous or stratified graft material.

Seyedin, et. al., in U.S. Pat. No. 4,434,094, describes the purification of a protein factor, which is claimed to be different than Urist's BMP molecule, responsible for the induction of chondrogenic activity.

Bell, in U.S. Pat. No. 4,485,097, assigned to Massachusettes Institute of Technology, describes a bone equivalent, useful in the fabrication of prostheses, which is composed from a hydrated collagen lattice contracted by fibroblast cells and containing demineralized bone powder. As this prosthetic structure is also a hydrated collagen gel, it has little strength of its own. The patentee mentions the use of synthetic meshes to give support to the hydrated collagen lattices to allow handling. Nevertheless, there is no indication of the clinical use of the material or measurement of its total physical strength.

Ries, et.al., in U.S. Pat. No. 4,623,553, describes a method for producing a bone substitute material consisting of collagen and hydroxyapatite and partially crosslinked with a suitable crosslinking agent, such as glutaraldehyde or formaldehyde. The order of addition of these agents is such that the crosslinking agent is added to the aqueous collagen dispersion prior to the addition of the hydroxyapatite or calcium phosphate particulate material. The resultant dispersion is mixed and lyophilized. The patent lacks any well known components which are known osteogenic inducers, such as demineralized bone matrix or extracted bone proteins.

Caplan, et. al., in U.S. Pat. No. 4,620,327, describes a method for treating implants such as biodegradable masses, xenogenic bony implants, allografts, and prosthetic devices with soluble bone protein to enhance or stimulate new cartilage or bone formation. These structures may then be crosslinked to immobilize the soluble bone protein or retard its release. While the osteogenic activity of these implants are described in detail, their physical strength is not mentioned.

The above review of the prior art reveals that none of the bone prosthetic materials which claim the ability to induce new bone formation (osteoinductive materials) possess high strength characteristics. Furthermore, of those materials which are described with enhanced strength, these materials consist solely of a crosslinked conjugates of collagen and inorganic mineral, which lacks the ability to stimulate the induction of new bone.

It is especially relevant that none of the above references address the need to bind the dispersed particulate or inorganic phase to the organic carrier matrix (i.e. collagen). As will be described below, the treatment of demineralized bone matrix or particles or inorganic particles, prior to complexation with an organic biopolymer, such as collagen, is extremely important in determining the physical strength characteristics of the bioimplant.

Furthermore, the ability to orient protein or peptide particles in a stable fashion within organic or natural polymeric matrixes permits the ability to release drugs, bioactiveproteins, and bioactive peptides in a controlled fashion.

SUMMARY OF THE INVENTION

Currently available or described compositions which contain demineralized bone matrix particles or conjugates of inorganic particles plus reconstituted structural or matrix proteins exhibit poor physical stability or physical strength when subjected to loads of any magnitude. Furthermore, due to the poor structural integrity of these materials, further processing into alternative shapes or sizes for actual clinical use to induce new bone formation in osseous defects is limited. One of the major objects of this invention is to describe a method of producing an osteogenic, biocompatible, composite which possesses unique strength properties. While many disclosures in the art describe the use of crosslinking agents to enhance the physical integrity of protein-based, conjugate, osteoinductive materials, this disclosure documents a precise method and procedure application which produces osteogenic graft materials of exceptional strength and physical integrity.

Furthermore, the basic concept described in this application may be adapted to create conjugates of natural biopolymers and inorganic bone minerals which display exceptional bonds between the inorganic particles and the polymeric matrix. The spacial stability of these particles is critical to their successful use clinically.

A further object is the creation of protein based structures which may release drugs or other agents in a controlled and stable fashion. The dimensional and physical stability of these conjugate material plays a significant role in the pharmacologic release properties of these materials. Hence, the physical strength and drug delivery capabilities are interrelated.

Two elements are germane to the observed properties of these novel compositions. First, the surface activation and partial crosslinking of the proteinaeous particles forms a reactive interface such that these particles bind in a stable fashion to the organic matrix, i.e. reconstituted collagen. This step is important with respect to enhanced physical properties. Second, inorganic particles may be bound to and stabilized within an organic or protein-based polymer by first creating a bound interface of calcium-binding protein or peptide to the particle. The modified particle is then bound to the matrix proteins via chemical crosslinking or activation methods. This method, as in the first case, significantly enhances the physical properties of these conjugates.

In summary, the primary of object of this application are:
1) A method for surface activating and/or partially crosslinking protein-based or protein coated particles to enhance their binding and reactivity to organic matrixes, including serum, plasma, naturally occurring proteins, and bone substrates.
2) To disclose a method and composition which induces bone when implanted in an animal or human and has early on stress-bearing properties not described in the prior art.
3) To disclose a method and composition of binding inorganic particles or particles which contain inorganic, mineral elements to a surrounding organic matrix such that a stable, stress-bearing conjugate results. The inorganic particles in such a conjugate are not easily displaced or dislodged from the matrix, as can be the case when the particles are simply added to the matrix without appropriate surface treatment.
4) Applying one of the above methods to stabilize drug-containing, protein-based particles within an organic or polymer matrix to effect a delayed or controlled release of the drug from conjugate material.

DETAILED DESCRIPTION OF THE PREFERRED EMBODIMENTS OF THE INVENTION

When particles which contain protein or amino acid components, such as protein microcapsules, finely divided particles of reconstituted collagen, demineralized bone matrix, or demineralized bone matrix extracted in chaotropic agents are partially crosslinked in a low concentration solution of glutaraldehyde, the surface of these particles become highly reactive, thus allowing an increased degree of bonding between the particle and an organic matrix or polymer, in which the particles may be dispersed. These structures, when dehydrated into a solid mass, display internal cohesive strength properties not found in simple combinations of the particles dispersed within the matrix component. If the glutaraldehyde is added directly to the matrix prior to addition of the particles and subsequent dehydration, very low levels of cohesive strength are developed. This is also true if the entire dehydrated conjugate matrix is crosslinked. The critical element to increasing the strength and internal cohesiveness protein-based particle/biopolymer matrix conjugated appears to be the partial crosslinking or surface activation of only the particles prior to complexation with the biopolymer organic matrix.

If bioactive particles, such as demineralized bone matrix, or drug containing particles are to be complexed, the conditions of surface activation and partial crosslinking are material. For example, crosslinking of demineralized bone particles above 0.25 weight percent glutaraldehyde destroys most of the osteoinductive capacity of the particles. At higher crosslinking levels, the particles will mineralized by the uptake of calcium phosphate, but will not induce new bone. Thus, the use of glutaraldehyde above 0.25 weight percent and, preferrably, below 0.1 weight percent, is a material condition in this invention.

The nature of the matrix effects the ultimate strength properties of the conjugate biomaterial, which is critical in clinical stress-bearing applications. For example, reconstituted collagen provides a matrix which demonstrates the unique and unexpected strength properties of this material. The method in which the collagen is reconstituted, however, can have a direct effect on the magnitude of the increased cohesive strength. This will be illustrated in the Examples which follow.

Agents other than glutaraldehyde may be used to enhance the surface binding of protein-based particles within a biocompatible matrix. For example, free and available carboxyl groups on the protein particle may be converted to amine groups via reaction with a water soluble carbodiimide in the presence of a diamine. These additional available amine groups can then react with glutaraldehyde in the partial crosslinking reaction. Alternatively, demineralized bone matrix particles can be immersed in solutions of tetracycline which, will enhance binding an organic biopolymer matrix. In addition, bone particles or partially demineralized bone particles may be demineralized in solutions of tetracycline.

Particles with inorganic components may be added to these osteogenic stress-bearing compositions, provided these particle makeup no more than twenty percent of the total weight of the particles. These inorganic component particles are bound to the biopolymeric organic matrix via functional molecules with calcium or hydroxyapatite binding functionality. In one embodiment, all the particles may be inorganic in nature and bound to the matrix in this fashion. The advantage here is enhanced strength as well as limiting the loss of particles from the matrix itself.

The increased binding between the particle and matrix constituents can also be advantageous in drug delivery. The method of dispersing a drug, protein, or peptide within the particle prior to crosslinking and surface activation permits the use of drug containing particles with reduced solubility to act as drug reservoirs within a biocompatible matrix. The nature of matrix can regulate the rate of drug release from the conjugate material.

The matrix biopolymer can be modified in a number of ways. For example, the hydrophilic or hydrophobic nature of the matrix may be altered by the addition of carbohydrates or lipids. The addition of acidic phospholipids to the matrix enhances the calcium binding capacity of the matrix. Additional macromolecules may be added to the matrix to achieve a particular biologic response. The addition of calcium hydroxide whether in a soluble form or as part of a protein-based particle, was found to increase the pH of matrix such that in-vitro bone collagen synthesis was increased in such an environment. Heparin may also be added.

Furthermore, crosslinking agents may be added to the matrix or subjected to the entire conjugate to further retard the degradation of the matrix and decrease its solubility. The degree of matrix degradation and its inflammatory response can also be controlled by the stabilizing affect of alkaline phosphatase.

Finally, a decided advantage of these compositions is their ability to be cast into definite shapes with good registration of surface detail. Due to their structure, there is much greater unformity in these compositions than is found in allogenic tissue. Furthermore a significant finding is the ability of these conjugate structures to be ground or milled by conventional means without gross breakdown of the entire matrix or the development of severe surface defects. This finding is significant since diagnostic techniques now allow the accurate three-dimensional representation of bony defects with the resultant milling of a graft material via CAD/CAM technology. There is no other processed, truely osteogenic, graft material which can be ground to precise specifications for insertion in a bony defect.

EXAMPLE ONE

Ten grams of demineralized bone matrix are milled in an A-10 mill to a uniform particle size ranging from 75 to 400 microns. The demineralized bone matrix particles are sieved to eliminate particles above 400 microns. Controlling the concentration of glutaraldehyde is material to maintaining sufficient osteoinductive activity of demineralized bone matrix particles. For example, glutaraldehyde crosslinking solutions of as low as 1.0 to 1.5 weight percent can reduce the residual osteoinductive activity of demineralized bone matrix to 10% or less. Glutaraldehyde crosslinking in aldehyde concentrations of 0.08 to 0.2 weight percent, however, only reduce the residual osteoinductive activity of demineralized bone matrix by 30 35 percent, leaving from a background osteoinductive activity of from 65 to 70 percent of uncrosslinked demineralized bone matrix particles. Therefore, control of the glutaraldehyde concentration used in this procedure is material to maintaining the biologic activity of processed demineralized bone matrix particles.

The range of glutaraldehyde used to partially crosslink and surface activate the demineralized bone matrix particle may range from 0.002 to 0.25 weight percent glutaraldehyde. The preferred range is from 0.005 to 0.09 weight percent glutaraldehyde. The partial crosslinking of demineralized bone matrix retards the resorption of the matrix in a non-inflammatory fashion, enhances the attachment of plasma proteins to the surface of demineralized bone matrix, and facilitates the attachment of the demineralized bone matrix to the organic collagen matrix of the bony surface of the osseous defect.

In this example, the demineralized bone particles are immersed in a 0.05 weight percent glutaraldehyde aqueous solution buffered with phosphate buffer to a pH of from 7.0 to 7.6. The glutaraldehyde solution is made isotonic by adding NaCl to a final concentration of approximately 0.9 weight percent. Alternatively, the glutaraldehyde solution may be buffered in the acid or the alkaline range. The glutaraldehyde solution may also be unbuffered consisting of only sterile distilled deionized water or sterile isotonic saline.

The demineralized bone matrix (DBM) particles are immersed in the solution of 0.05 weight percent glutaraldehyde in neutral phosphate buffered isotonic saline for 12 hours with constant agitation at 4 degrees centigrade. At the end of the incubation period, the particles are filtered from the crosslinking solution and washed particles are filtered from the crosslinking solution and washed once with phosphate-buffered isotonic saline. The DBM particles prepared are dried under sterile conditions and then sterilized by an appropriate method, such as ethylene oxide, gamma radiation, or electron beam sterilization.

These activated particles may be placed directly in an osseous defect or alternatively, complex with an organic biopolymer as described in later Examples.

EXAMPLE TWO

The demineralized bone matrix particles are extracted with a chaotropic agent to remove all bioactive or immunologic elements. Allogenic or heterogenic particles treated in this fashion make excellent delivery particles for the complexation of drugs, peptides, or proteins. After swelling in acid or alkaline solutions the extracted demineralized bone particles are immersed in the agent to be bound and released from the particle. The particle is then dried and crosslinked in a controlled fashion as described in Example One. The specific illustration below describes the use of this method.

Ten grams of demineralized bone matrix particles, with a particle size of from 75 to 400 microns (preferably from 150 to 400 microns), are immersed in guanidinium hydrochloride buffered with 50 millimolar phosphate buffer, pH 7.4. The particles are maintained in this extraction medium at 4 degrees centigrade for 10 to 15 hours with gentle agitation. Optionally, protease inhibitors such as 0.5-millimolar phenylmethyl-sulfonyl fluoride, 0.1 molar 6-aminohexanoic acid, are added to the extraction medium.

At the end of the extraction period, the extracted demineralized bone matrix particles are removed from the extraction solution by vacuum filtration or centrifugation at 800 to 1000 rpm. The extracted demineralized bone matrix particles (EDBMP) are washed 10 to 20 times with neutral sterile phosphate buffered saline. The particles are then dialyzed against several changes of neutral phosphate buffered saline to remove any remaining amounts of the chaotropic agent.

A suitable bioactive peptide or protein may be absorbed onto EDMB particles. In this Example thyrocalcitonin is used in this fashion. A one gram fraction of the EDBM particles are immersed in a 100 ppm solution of thyrocalcitonin in sterile normal saline. The particles are maintained in this solution for 24 to 72 hours with periodic gentle agitation.

The complex EDBM-thyrocalcitonin particles are separated by vacuum filtration and rinsed once to remove any excess peptide. The EDMB-thyrocalcitonin particles are immersed in a low concentration glutaraldehyde crosslinking solution as described in Example One. The particles are dried and sterilized as describe in that example. When tested in-vitro and in-vivo, particles showed a time dependent release of the peptide.

Other peptides and proteins, such as Bone Morphogentic Protein, Insulin-like growth factor. Epidermal Growth Factor, Nerve Growth Factor, Human Growth Hormone, Bovine Growth Hormone, or Porcine Growth Hormone, are several examples of peptides or proteins that can be carried by the EDBM matrix particles. Conventional drugs, such as tetracycline or other antibiotics, may also be delivered via this system.

EXAMPLE THREE

Protein-based microcapsules can be fabricated and then partially crosslinked under controlled conditions so that they become reactive and bind to an organic biopolymer matrix under controlled conditions. As an illustration, a gelatin-protein microcapsule is fabricated and partially crosslinked to surface activate the microcapsule.

Two and one-half grams of U.S.P. gelatin and 25 milligrams of Bone Morphogenetic Protein (purified as described by Urist in the above) are mixed in 8 milliliters of sterile distilled water at 60 degrees centigrade. Following solubilization of the gelatin and complexation with Bone Morphogentic protein (BMP), 2 milliliters of 1 millimolar phosphate buffer, pH 7.4 is added to the gelatin-BMP solution with constant stirring. This solution is maintained at 55 to 60 degrees centigrade. In a separate container, one hundred milliliters of an oil phase is prepared by combining 20 milliliters of petroleum either with 80 milliliters of mineral oil. This solution is heated to 55 to 60 degrees centigrade.

The gelatin-BMP solution is added to the oil phase with rapid stirring over a 15 second period leading to the formation of gelatin-BMP microspheres. Upon chilling to 2 to 4 degrees centigrade, the gelatin-BMP spheres jelled into beads. The oil phase of the solution is removed by vacuum filtration. The beads were washed with petroleum ether and diethyl ether.

The microspheres so obtained are then crosslinked as described in Example One. In this Example, the microspheres are crosslinked in 0.03 weight percent glutaraldehyde in neutral phosphate buffered isotonic saline. The microspheres are filtered by vacuum filtration and rinsed once with neutral sterile isotonic saline. The spheres are dehydrated and stored dry. Alternatively, the spheres may be complexed with an organic biopolymer matrix to form a stress-bearing bioprosthesis.

EXAMPLE FOUR

Ten grams of milled bone powder (not demineralized), which has been defatted and extracted with an organic solvent, such as diethyl ether, is immersed in a solution of tetracycline HCl at a concentration of from 5 micrograms per milliliter to 50 milligrams per milliliter. Alternatively, the milled bone powder or particles is first partially demineralized in a 0.05 to 0.3 molar solution of HCl at 4 degrees centigrade for from 30 minutes to 5 hours. These partially demineralized bone particles are then contacted in a solution of tetracycline HCl as specified above.

The particles are immersed in a 10 micrograms per milliliter solution of tetracycline HCl for from 1 to 24 hours at 4 degrees centigrade. At the end of the immersion period, the particles are rinsed once in neutral buffered isotonic saline. The particles are collected and dried or lyophilized. The particles in this instance are collected, dried under ambient conditions and lyophilized.

As an additional procedure, the dried particles are partially crosslinked with glutaraldehyde as described in Example One. As will be described in Example 6, these tetracycline treated demineralized bone matrix particles are subjected to other means of chemical group activation such as via carbodiimide activation of surface carboxyl groups and reaction with an amine or diamine.

EXAMPLE FIVE

Other protein containing particles are fabricated from pulverized reconstituted collagen particles. As an example, collagen-tetracycline conjugates sponges are fabricated by adding tetracycline HCl to an acid solubilized reconstituted collagen dispersion. The final tetracycline concentration is 10 to 50 micrograms per milliliter and the collagen concentration is from a 0.5 weight percent dispersion to a 3.5 weight percent dispersion. The collagen is solubilized with acetate or hydrochloric acid in the acid range or sodium hydroxide in the alkaline range. The pH of the collagen dispersion is adjusted to neutrality or near neutrality by repeated dialysis against sterile distilled water or phosphate buffered saline.

After the collagen dispersion is adjusted to near neutrality, the appropriate drug, peptide, or protein is added to the collagen dispersion and agitated to assure complete mixing. In this example the collagen-tetracycline composition is poured into a cylindrical mold and allowed to stand for 24 hours in a sterile laminar flow box to allow initial gellation. After gellation, the dispersion is placed on the minus 60 degree shelf of a lyophilizer and freeze-dried to form a sponge material. The sponge conjugate material is removed from the lyophilizer and placed in a controlled dry-heat oven at a temperature of form 45 to 80 degrees centigrade. The heat stability of the molecule conjugated to the collagen determines the appropriate temperature. The dried sponge is removed and milled to a powder in an A-20 mill. The collagen-tetracycline particles produced are then surface activated and partially cross linked.

EXAMPLE SIX

The binding and covalent attachment of protein-based particles protein microcapsules, demineralized bone matrix particles, or protein conjugated inorganic particles, are enhanced by increasing the number of surface binding sites. This increase in binding sites accomplished by the following procedure.

Ten grams of demineralized bone matrix particles are obtain with a particle size of from 50 to 400 microns. The particles are immersed in a water soluble carbodiimide, 1-ethyl-3-(3-dimethylaminopropyl)carbodiimide is varied between 0.005 molar to about 0.1 molar preferably about 0.05 molar to about 0.1 molar preferably about 0.05 molar in a isotonic salt solution. The pH of the carbodiimide solution was maintained between about 4.7 and about 5.2 by the addition of HCl. Ethanol and other organic compounds, such as mannitol are added from time to time to alter the dielectric constant of the crosslinking solution. Alternatively, the ionic strength is increased by the addition of NaCl from about 0.1 molar to 1.0 molar. Similar modification is undertaken from time to time with the glutaraldehyde crosslinking procedures.

The reaction with the carbodiimide proceeds from about 20 minutes up to 12 hours or more. In this particular example, the reaction time is 2 hours and the reaction is carried out at four °C., the surface activated demineralized bone particles are then contacted with an amine or diamine. Materials with amine functional groups include amino acids, polyamino acids, globular proteins such as albumin and gelatin, fibrillar proteins such as collagen and elastin. Alternatively, in this instance a diamine, namely hexanediamine, is used to react with the carbodiimide activated particles. The hexanediamine permits the increase of free available amine binding sites for activation by glutaraldehyde. The hexanediamine solution contains from 0.01 weight percent to about 2.0 weight percent diamine. The optimal diamine concentration is approximately 0.1 to 0.5 weight percent in a neutral buffered saline solution at pH 7.4. The contact time is from 2 to 10 hours with the usual time being four hours.

The particles are removed from the diamine solution by filtration and are rinsed several times with neutral buffered saline to remove excess diamine. The demineralized bone particles are added to a crosslinking solution of glutaraldehyde with an aldehyde concentration of from 0.001 weight percent to 0.25 weight percent. The method used is identical to Example One and the concentration of glutaraldehyde is 0.05 weight percent. The partial crosslinking occurs at 4° C. in a neutral buffered isotonic saline solution. The crosslinking solution time is 8 to 12 hours. The particles filtered from the solution and are washed once with buffered neutral isotonic saline. The particles are dried and at this point can be used for binding in an organic biopolymer matrix to produce a stress-bearing bone graft, as described herein. Alternatively, the particles are lyophilized and sterilized by either ethylene oxide, liquid sterilizing solution, gamma radiation, or electron beam sterilization.

EXAMPLE SEVEN

An aqueous collagen dispersion is made from a high purity, medical grade, sterile powdered collagen. The constituted collagen dispersion is made at 2.5 weight percent collagen by solubilizing the collagen powder in a 0.01 N acetic acid buffer. The collagen powder is added, from time to time in concentrations ranging from 0.5 weight percent to 2.5 weight percent. Other organic acids, such as lactic acid or inorganic acids, such as hydrochloric acid, are also used from time to time to facilitate the swelling of the collagen matrix.

The acid dispersion of the collagen is mixed with moderate agitation and stored overnight to permit thorough swelling of the collagen gel. The collagen dispersion is vigorously agitated and sheared in a Waring Blender under medium to high speed using 3 to 5 intermittant, 30 second mixing periods. The collagen dispersion is then poured into an appropriately sized centrifuge tubes and centrifuged at 800 rpm to remove entrained air within the collagen dispersion. The dispersion is then dialyzed against a solution of sterile distilled water. The collagen dispersion is repeatedly dialyzed against fresh exchanges of sterile distilled water until the pH of the collagen dispersion is in the range of pH 5.3 to 7.0. On occasion to obtain a dispersion with a pH of from 6.8 to 7.6 in an efficient manner, the collagen dispersion is dialyzed against a buffer solution such as neutral phosphate buffer. The dialyzed collagen dispersion is collected and placed in a container at 4 degrees centigrade. The dispersion serves as a matrix material.

Two types of demineralized bone matrix particles are utilized in this procedure. The first type are normal demineralized bone particles without surface activation with glutaraldehyde. The second type are particles of demineralized bone matrix identical to the first group except they are activated by partial crosslinking in glutaraldehyde as described in Example One. These two systems are described as follows:

1) Demineralized bone particles at 85 weight percent are dispersed in the aqueous collagen matrix; placed in a cylindrical mold and cast by forced air dehydration at ambient conditions. The conjugate cylinders are retained for physical testing.

2) Demineralized bone particles, identical to above (1) are activated in glutaraldehyde as described in Example One. These particles are then dispersed at 85 weight percent in the aqueous collagen matrix. The conjugate is placed in a cylindrical mold and cast by forced air dehydration at ambient conditions. The conjugate cylinders are retained for physical testing.

To better understand the action of glutaraldehyde in these matrix particle conjugates, three other methods of addition of 0.5 weight percent glutaraldehyde are also employed. These are 3) Demineralized bone particles at 85 weight percent are dispersed in the collagen matrix. Neutral buffered glutaraldehyde is added to the aqueous dispersion so that the final concentration is 0.5 weight percent. The conjugate is placed in a cylindrical mold and cast by forced air dehydration at ambient conditions. The conjugate cylinders are retained for physical testing.

4) Neutral buffered glutaraldehyde is added to the collagen dispersion prior to the addition of demineralized bone matrix particles (unactivated). The glutaraldehyde is added so that its concentration with respect to the total weight of the conjugate would be 0.5 weight percent. The demineralized bone matrix particles are then added with mixing at a weight ratio of 85 weight percent. The conjugate is placed in a cylindrical mold and cast by forced air dehydration at ambient conditions. The conjugate cylinders are retained for physical testing.

5) Conjugate cylinders are fabricated as described for System (1) above, but are then immersed in a neutral buffered solution of 0.5 weight percent glutaraldehyde at 4 degrees centigrade for 72 hours. The cylinders are removed and washed repeatedly in neutral phosphate-buffered isotonic saline. The cylinders are replaced in their original molds and dried by forced air dehydration under ambient conditions. The conjugate cylinders are retained for physical testing.

The following table displays the results obtained with the physical testing of the different systems. The cylinders are tested for diametrial tensile strength in an Instron Tester at constant loads 5 or 20 kiligrams, depending on the strength of the material. The dimensions of the cylinders are measured prior to testing and all cylinders are tested on their sides as is usual for the diametrial internal cohesive strength of a material.

|  | SYSTEM | | | | |
| --- | --- | --- | --- | --- | --- |
|  | 1 | 2 | 3 | 4 | 5 |
| Force Applied Strain Profile | 5 Kg Sponge-like | 20 Kg Resistant to load with yield point | 5 Kg Sponge-like | 5 Kg Sponge-like | 5 Kg Sponge-like |
| Diametrial Tensile Strength | <2.5 psi | 90 psi | <2.5 psi | <2.5 psi | <2.5 psi |

Note:
Collagen-demineralized bone particle compositions at or above 90 weight percent bone particles to collagen fail to aggregate into a cohesive mass and spontaneous disintegrate under any degree of force.

EXAMPLE EIGHT

The nature of the matrix biopolymer also has a definite effect on the internal cohesive strength of the material and its ultimate strength properties. The procedure below illustrates the fabrication of a collagen-based material which is adhesive to itself or other bone compositions, is hemostatic, and is osteogenic.

Ten (10) grams of sterile collagen powder (Collastat) is mixed in 100 milliliters of 0.1 N HCl with stirring-bar agitation. After 15 minutes of agitation, collagen dispersion is diluted from 10 weight percent to 5 weight percent by a two-fold dilution with sterile distilled water. This results in a final acid concentration of 0.05 N HCl and a final pH of 4.1 to 4.3.

Four point three (4.3) grams of milled demineralized bone powder (particle size 125 microns or less; MW 0.250 sieve) are added to the collagen mixture. After thorough stirring the 5 percent dispersion is mixed in a Waring Blender for 5 to 10, 20 second agitations to increase the dispersion viscosity. The thickened solution is poured into centrifuge tubes and spun in a table-top centrifuge at 400–600 rpm for 5 minutes to remove air and concentrate the collagen.

Excess fluid supernatant is removed by pipetting and the collagen conjugate fraction is collected into a single volume (approximately 170 milliliters). This collagen-demineralized bone dispersion is stored at 4 degrees centigrade for at least one hour to check for consistency and the presence of phase separation. The pH of the mixture is 4.50 to 4.57.

The collagen mixture is transferred to dialysis tubing (Spectrapor. 12,000 to 14,000 molecular weight cut-off) and dialyzed overnite against sodium phosphate buffer 0.02 molar pH 7.4. The collagen-DBP dispersion is removed from the dialysis tubing using aseptic technique. The dispersion is homogeneous and shows no evidence of separation. The pH of the dialyzing solution is 6.5. The pH of the collagen dispersion is 5.00 to 5.12.

The dialyzed collagen-DBP dispersion is collected, placed in a 250 milliliter centrifuge bottle, then spun at 800 rpm for 10 minutes. The clear supernatant is collected and checked for pH which is 5.10.

The collagen-DBP dispersion is placed in sterile petri dishes and frozen, under aseptic conditions, at minus 40° C. under vacuum, the vacuum is maintained for 18 to 24 hours to assure complete dehydration. The resultant foam-like sponge material is placed in an A-10 mill and milled into a powder. The powder is divided into equal aliquots and bottled. The bottles of collagen-DBP powder are sterilized under ethylene oxide for 2 and ½ hours. The bottles are aerated under vacuum for at least 24 hours and then sealed under vacuum.

The resultant material is hemostatic in that it promotes the clotting of blood.

EXAMPLE NINE

The collagen-demineralized bone particle powder, as described in Example Eight is reconstituted in a 5 mM solution of sodium phosphate buffer, pH 8.0. Approximately 0.2 grams of the powder is hydrated with 1 milliliter of the buffer and mixed to assure complete mixing. Demineralized bone particles, average particle size 250 microns are activated and partially crosslinked as described in Example One. A weight of 0.10 grams of these particles are added to the buffer-collagen conjugate dispersion with gentle mixing. The mixture is placed in a cylindrical mold and dehydrated by forced air under ambient conditions. The resultant disc dried very rapidly, i.e., within 4 to 10 hours. If the mass is lyophilized, a more porous structure results. The detail of the mold is well reproduced on the cylinder. Cylinders demonstrate a smooth surface appearance and have sufficient integrity to be milled or ground to precise shapes with surgical burs or grinding wheels in low or intermediate speed handpieces. The cylinders so produced are tested for diametrial tensile strength at 20 kiligram constant load. The results are as follows:

| SYSTEM 6 | |
| --- | --- |
| Force Applied | 20 kg load |
| Strain Profile | Linear, elastic behavior with increased modulus in tension |
| Diametrial Tensile Strength (PSI) | 279 to 320 psi |

EXAMPLE TEN

Other drugs, proteins, or peptides are added to the matrix phase of these compositions which contain activated particles. For example, a purified or recombinant bone morphogenetic protein, as described by Urist in U.S. Pat. No. 4,294,753 is added to the matrix prior to the addition of activated particles or microcapsules. As the stability of the conjugate does not rely on addition of glutaraldehyde to the bone matrix, the chance of inactivating the BMP molecular is reduced. The conjugate material can be used in its aqueous form, however, in this instance the activated demineralized bone particles-collagen-BMP conjugate is dehydrated under ambient conditions, as described earlier. Another sample is dehydrated and then lyophilized at minus 40 to minus 60 degrees centigrade.

Another conjugate, made in identical fashion with respect to order of addition of components, consist of activated demineralized bone particles-collagen and tetracycline HCL. This conjugate is dehydrated and lyophilized. Other proteins and peptide growth factors are evaluated when complexed with the matrix phase of this novel, cohesive compositions.

EXAMPLE ELEVEN

The activated and partially crosslinked protein particles, microcapsules or demineralized bone matrix particles whose methods of surface activation were described in above Examples, are added to viscous mixtures of blood proteins, glycoproteins, or cell component fractions.

Specifically, 0.5 grams of activated demineralized bone matrix or bone matrix particles are removed from the container in which they are sterilized. In this instance, the bone is being used to fill an osseous defect in a laboratory animal. Five milliliters of the animal's blood is withdrawn by ventipuncture. The blood is spun at 800 to 1000 rpm in a table-top centrifuge to spin-down platelets, white blood cells and red blood cells. The blood is drawn into a plain vial which does not contain any type of anticoagulant. After the cellular components of the blood are pelleted, the supernatant containing serum is withdrawn carefully with a pipette. The serum is added to the activated demineralized bone particles so that the particles are evenly coated. The ratio of activated bone particle to serum or plasma can vary from 20 to 95 percent by weight. The conjugate is placed into the bony defect such that it is filled completely. The defect is gradually replaced with new bone over a period of 6 to 12 weeks.

The identical procedure is undertaken with another research animal except this time the blood is drawn into a heparinized tube and plasma is obtained after centrifugation. This blood plasma is combined with the activated blood particles in a manner identical to the above.

In certain instances, such as large osseous defects or non-unions, it is beneficial to add bioactive molecules or antibiotics to the serum or,plasma fraction. Rabbit bone morphogenetic protein is purified from rabbit demineralized bone matrix, using a method described by Urist in U.S. Pat. No. 4,294,753. The purified BMP is added to the plasma so as to constitute about 0.5 to 3 percent by weight. After mixing the lyophilized protein into the plasma and dispersing it thoroughly, the activated demineralized bone particles are mixed into the BMP-plasma at a weight ratio of 80 to 90 parts of particles to 10 to 20 parts of plasma.

Another laboratory animal is presented with a bone injury with possible bacterial contamination. Blood is drawn and plasma obtained as previously mentioned. To the plasma is added a powder tetracycline hydrochloride salt at a concentration of 5 to 25 micrograms per milliliter. The antibiotic is mixed thoroughly in the plasma and the plasma mixed with activated demineralized bone particles at a weight ratio of 80 to 90 parts particles to 10 to 20 parts plasma-tetracycline.

EXAMPLE TWELVE

The proteins which constitute the matrix can be further modified by the addition of phospholipids. In particular, reconstituted collagen and acidic phospholipids demonstrate together an enhanced uptake of calcium as compared to collagen matrixes without conjugated acidic phospholipids.

A 2.5 weight percent collagen dispersion at a pH of 5.0 to 5.5 was used for the addition of an acidic phospholipid, L-alpha-phosphatidic acid, dipalmitoyl, is added to the above reconstituted collagen dispersion at from 0.01 milligrams per milliliter collagen to 10 milligrams per milliliter collagen. The conjugate dispersion is dehydrated at ambient temperatures and lyophilized. Alternatively, activated protein particles, microcapsules, or demineralized bone matrix particles are added to the conjugate aqueous dispersion as described within this disclosure.

EXAMPLE THIRTEEN

A reconstituted collagen matrix can be further modified by the addition of an alkaline source of calcium ions. For example a reconstituted collagen dispersion with a collagen composition of 0.5 to 2.5 percent by weight and a pH of 5.0 to 5.5 is dialyzed against a saturated solution of calcium hydroxide in sterile distilled water. When the pH of the collagen dispersion reaches 10 to 10.5 the collagen dispersion is removed from the alkaline solution, placed in an appropriate sized mold and lyophilized to form a sponge. Another aliquot of the collagen-calcium hydroxide is combined with activated demineralized bone particles and mixed to thoroughly disperse the particles in the alkaline matrix. The conjugate is dehydrated and lyophilized to form a stress-bearing sponge material.

These collagen-calcium hydroxide conjugates demonstrate rapid release of the calcium and hydroxide ions and load only sufficient amounts of hydroxide ions to slightly adjust the pH.

EXAMPLE FOURTEEN

A calcium hydroxide (CaOH)/collagen-gelatin microbead is fabricated using the following method. A reconstituted collagen dispersion at neutral or acidic pH is made as described in prior Examples. Powdered calcium hydroxide is slowly added to the dispersion until a pH such that a collagen to gelatin conversion was evident. The pH necessary to effect this conversion is approximately 11.0 or above. The visual effect at this conversion was quite noticable, as the collagen dispersion loses all its translucency and becomes opaque and chalky.

The colloidal dispersion can be formed into microbeads by immersion in an oil phase, as described in Example Three. Nevertheless, in this example, the collagen-CaOH gelatin dispersion may be dried by lyophilization at minus 40 minus 60 degrees centigrade. Dehydration at ambient temperatures also yields a solid mass.

This mass is milled and pulverized is into fine particles. The particles are partially cross-linked in a 0.05 weight percent glutaraldehyde solution at a pH of 7.8. After rinsing once, the activated collagen/gelatin-CaOH particles are added to an alkaline collagen dispersion containing calcium hydroxide. This mixture may be lyophilized or dehydrated. However, activated demineralized bone particles may be added in a weight percent range of from 10 to 85 weight percent.

EXAMPLE FIFTEEN

A collagen-calcium phosphate conjugate is derived as described by Cruz in U.S. Pat. No. 3,767,437. A reconstituted collagen dispersion at a pH of 3.5 to 4.5 in sodium acetate is dialyzed first against 3 to 7 changes of deionized water and then dialyzed against a saturated solution of calcium hydroxide for 2 to 5 changes. The collagen-CaOH solution is then dialyzed against a solution of phosphoric acid adjusted to pH 3.0 to 4.0. The dialysis for 2 to 6 changes resulted in a Collagen-Calcium Phosphate conjugate. The dispersion is lyophilized or dehydrated under an ambient conditions. The resultant mass is pulverized under moderate force. The resultant particles are sieved to a uniform particle size of 50 to 1000 millimicrons. The particles are dried and placed in a 0.08 glutaraldehyde solution also contains 8 mM calcium phosphate buffer. The particles are filtered and rinsed once with sterile distilled water.

The partially crosslinked, activated particles are added to a reconstituted collagen dispersion with moderated mixing and agitation. The dispersion can be left in a viscous gel-state, lyophilized, or dehydrated at ambient conditions. The resultant dried mass has a diametrial tensile strength greater than one hundred PSI.

EXAMPLES SIXTEEN

Collagen-calcium phosphate particles, prepared and activated as described in Example Fifteen, are added to a composition derived as described in Example Seven, System No. 2. Inorganic particles are added to collagen matrix phase, so that no more than 20 weight percent of the entire conjugate is composed of the protein/inorganic particles. The entire mass is cast and dehydrated as described in the earlier Examples.

EXAMPLE SEVENTEEN

Collagen-calcium phosphate particles, prepared and activated as described in Example Fifteen are added to a composition derived as described in Example Nine. The inorganic particles are added so that no more than 20 weight percent of the entire conjugate is composed of the protein/inorganic particles. The entire mass is cast and dehydrated as described in the above Examples.

EXAMPLE EIGHTEEN

Collagen-calcium phosphate particle conjugate derived from either hydroxyapatite or tricalcium phosphate particles even when crosslinking agents such as glutaraldehyde in low concentrations are added to the collagen matrix, demonstrate very low tensile strengths i.e., on the order of 30 psi or less. A method is described in this example to provide collagen-hydroxyapatite or collagen-tricalcium phosphate conjugates with enhanced strength and reduced plucking of the inorganic particles from the matrix.

An acid dispersion of reconstituted collagen is made in the acid pH range using 0.05 acetic acid as described earlier. The collagen dispersion is made at 0.75 weight percent collagen sheared in a Waring Blender and dialyzed against sterile isotonic saline until the pH of the dispersion reaches a range of 4.0 to 5.5. Tricalcium phosphate particles medical grade and sterile with a particle size of 50 to 150 millimicrons are added to the dispersion with moderate mixing. The dispersion is degased under vacuum with moderate agitation. The dispersion is placed in a dialysis tube and dialyzed against 0.01 molar phosphate buffer at pH 8.0. The dialysis tube is periodically removed aseptically and inverted several times to prevent separation of the mineral phase. After 24 to 48 hours of dialysis the dispersion is removed from the dialysis tubing, poured into a stainless steel mold and lyophilized at between minus 40 and minus 60° C.

At the conclusion of lyophilization the sponge like mass is cut into about 0.5 cm square cubes and milled carefully at low settings in an A-10 mill so as to provide a group of collagen-mineral particles on order of about 250 to 550 microns. The particles are activated in a manner consistent with one of the embodiments of the invention. Specifically, in this example, the conjugate particles are immersed in a neutral buffered isotonic solution of bout 0.08 weight percent glutaraldehyde. The concentration of the glutaraldehyde was varied from 0.001 to 0.25 weight percent glutaraldehyde. The conjugate particles are activated for about 8 to 12 hours at 4 degree centigrade. The particles are removed by vacuum filtration and washed once in neutral buffered isotonic saline.

The activated protein-coated mineral particles are added to a reconstituted collagen dispersion of one to 2.5 percent by weight collagen, with a pH of from 3.5 to 5.0. The activated particles are added to the dispersion in a weight range of from 25 to 85 percent by weight. The preferred range is from 40 to 75 percent by weight. The activated protein-mineral particle/reconstituted collagen conjugate is poured into a stainless steel mold and dehydrated at ambient temperatures with forced recirculated air. The conjugate, once dehydrated may be lyophilized at minus 40 to minus 60° C.

Another conjugate of this type is cast except that prior to dehydration, a bioactive protein, peptide, or drug is added to the matrix, as has been described in earlier Examples.

EXAMPLE NINETEEN

While a stable coating of reconstituted collagen can be formed in a continuous adherent layer on the surface of an inorganic particle a preferred method is to form multiple chelation links between the calcium, rich surface and the protein-based surface layer.

Particles of a calcium phosphate ceramic material, namely tricalcium phosphate particles with a size of about 100 millimicrons are immersed in a 10 ppm solution of L-y-carboxyglutamic acid. The particles are incubated in this solution for 24 to 48 hours 4° C. The particles are removed from the solution dried under ambient conditions and immersed in about a 0.5 to 1 weight percent collagen dispersion containing about 10 to 50 ppm of L-y-carboxyglutamic acid. The particles are agitated gently in this dispersion filtered from the dispersion then placed in a 0.15 molar NaCl solution containing 0.05 molar sodium phosphate buffer adjusted to pH 7.4 with dibasic and tribasic sodium phosphate. After 15 minutes to one hour in this solution. the collagen coated particle is partially crosslinked in a 0.075 weight percent solution of glutaraldehyde for 8 to 10 hours.

The particles are removed from the glutaraldehyde solution by filtration then rinsed once in sterile saline solution. Once activated some of these particles are used directly in osseous defects. Alternatively, some of the activated particles are mixed into a 1 weight percent dispersion of reconstituted collagen. The particles are mixed and agitated to assure a uniform dispersion. The gel so obtained is used in certain osseous defects. Alternatively, the collagen-particle dispersion is lyophilized or dehydrated under forced air under ambient conditions. The resultant material is sterilized with ethylene oxide, gamma radiation, and/or by immersion in a 0.2 percent buffered glutaraldehyde solution.

EXAMPLE TWENTY

In place of the L-y-carboxyglutamic acid disclosed in Example Nineteen, the sodium salt of poly-L-glutamic acid or the random copolymer of L-glutamic acid, which contains at least one lysine in its repeating structure, may be used to coat the calcium phosphate particle prior to complexation with reconstituted collagen. In this procedure, the particles are mixed and agitated within the polyamino acid solution, then under ambient conditions the particles are dehydrated or alternatively, lyophilized. The coated particles are mixed in a reconstituted collagen dispersion and again dried to provide a uniform coating. The coated particles so produced are partially crosslinked in 0.05 weight percent neutral buffered glutaraldehyde for about 10 to 12 hours at 4° C. The particles are vacuum filtered from the activating solution and dried. The particles are then used as described within the embodiments of the invention. Alternatively, the polyamino acid coated particles once dried may be added to a reconstituted collagen dispersion which contains about 0.05 to 0.1 weight percent glutaraldehyde. The entire conjugate may be dehydrated or lyophilized, then milled to a powder if further complexation is intended.

EXAMPLE TWENTY-ONE

System No. 2 of Example Seven described the fabrication of a reconstituted collagen/activated demineralized bone matrix conjugate with improved internal cohesive strength. The weight percentage of activated particles is demonstrated to be useful in the range of 5 to 85 weight percent of the conjugate. Nonactivated particles can be added to matrix in weight percent ranging from 0 to 95 percent of the total conjugate weight. If the non-activated or activated particles are inert, inorganic particles, specifically, tricalcium phosphate hydroxyapatite, their weight percent does not exceed 20 weight of the total conjugate mass.

EXAMPLE TWENTY-TWO

Example Nine described a cohesive stress-bearing conjugate which is composed of an adhesive collagen-demineralized powder which is hydrated and admixed with an additional 20 weight percent of activated demineralized bone particles. This composition is comprised of 30 weight percent original unactivated particles plus twenty weight percent activated demineralized bone particles (average particle size 150 microns). The percentage of activated demineralized bone particles is from time to time, increased up to 50 weight percent of the total mass. Other conjugates are admixed to contain up to 20 weight percent (with respect to the total conjugate mass) of activated or non-activated inert inorganic particles consisting of particles of tricalcium phosphate or hydroxyapatite with a particle size range of 20 to 750 millimicrons, with the preferred range being 20 to 150 millimicrons the total weight percent of particles of any type greater than 85 percent of the total mass.

EXAMPLE TWENTY-THREE

The matrix component of the above examples may contain from a non-fibrillar collagen group, such as gelatin. Sufficient gelatin with a Bloom strength of at least 200 is added to the reconstituted collagen so that no more then 10 weight percent of matrix consists of gelatin.

EXAMPLE TWENTY FOUR

Polyamino acid microcapsules may be used to form protein-based, partially crosslinked particles as described in Example Three. The same procedure is followed except that a viscous solution of poly-l-lysine is used instead of gelatin. The other exception to the procedure is that the poly-L-lysine is used instead of gelatin. The other exception to the procedure is that the poly-L-lysine is warmed only to 37 to 43 degrees centigrade.

EXAMPLE TWENTY-FIVE

Other types of inorganic particles can be activated and reacted with collagen, gelatin, polyamino acid or polyalkenoic acids to form rigid, stress-bearing implants and cements. Aluminosilicate glasses, which contain varying amounts of calcium fluoride, are used for stress-bearing cements and implantable bone replacement structures.

These hard-setting cements formed from the reaction of powders and liquids. Specifically, milled aluminosilicate glass, designated G-309 or G-385 are provided. The reactant liquid consists of from 35 to 55 percent polyacrylic acid, molecular weight from 15,000 to 60,000 and from 2 to 35 weight percent reconstituted collagen and the balance distilled, deionized water.

The powder and liquid are mixed at a powder to liquid ratio of from 1.4 to 3 grams per milliliter liquid. The working time for the cement is about 1 minute 45 seconds to 2 minutes 45 seconds and the final set from 5 minutes 30 seconds to 6 minutes 45 seconds.

EXAMPLE TWENTY SIX

The reconstituted collagen-glass ionomer cements are varied by the addition of from 0.01 to 3 percent glutaraldehyde into the liquid component as described in Example Twenty-Six. The inclusion of glutaraldehyde shortens the working/setting time and produces a stronger cement as determined by physical testing.

EXAMPLE TWENTY SEVEN

The liquid component as described in Examples Twenty-Five and Twenty Six can be further modified by the addition or substitution of polyamino acids for the polyalkenoic acids in the liquid component. For the entire polyacid component of the liquid may be replaced with poly-L-glutamic acid. Alternatively, from 5 to 45 weight percent of the liquid component may consist of a polyamino acid, namely, poly-L-glutamic acid, poly-L-asparatic acid, poly-L-lysine, homopolymers or random co-polymers of these or any polyamino acid may be added to the liquid component. combinations of these polyamino acids polymers vary the setting time and the ultimate physical strength of the cement or implant.

EXAMPLE TWENTY EIGHT

Bone Morphogenetic Protein and/or bone proteins extracted from demineralized bone matrix may be incorporated into uniform unilamellar liposomes for controlled delivery to osseous defects. The procedure for incorporation of the bioactive proteins onto and into the membrane bilayer is described below.

A phospholipid, 1-palmitoyl-2-oleoyl-phosphatodyl-chlorine, is dispersed in an aqueous (sterile distilled water) phase by sonication and then mixed with lyophilized BMP such that the protein to lipid mass ratio to produce unilamellar BMP liposomes of optimal size (high encapsulation efficiency) is in the range of 1:2 to 1:3 with the optimal ratio being 1:2.5.

The resultant mixture is dried under nitrogen in a rotating flask. The dried sample is then rehydrated in aqueous medium under nitrogen with gentle rotation of the flask. The resulting unilamellar liposomes where separated from the free morphogenetic protein by chromatography through a B-4 or G200 Sephadex column.

The BMP-liposomes are stored at 4° C. or alternatively, lyophilized. Prior to implantation reconstituted collagen sponges allogenic bone autogenous bone grafts or demineralized bone matrix can be soaked in the liposome preparation to stimulate osteogenesis. Alternatively, the BMP-liposome can be mixed with an aqueous collagen dispersion for direct placement or injection to the wound site, or added to the matrix phase described in embodiments of this invention.

EXAMPLE TWENTY-NINE

Bone morphogenetic protein and/or extracted bone proteins can be entrapped in the patient's own red blood cells by resealing the cell ghosts in the presence of the bioactive proteins. This permits a highly biocompatible delivery system for BMP delivery to a wound site.

Fresh heparin-treated whole blood (about 50 milliliters) is centrifuged at 1000 gs for 10 minutes. The plasma and buffy coat is removed and the cells are washed three times in cold (4 degrees centigrade) Hanks Basic Salt Solution (HBSS). The packed cells are mixed rapidly with twice their volume of cold hemolysing solution consisting of distilled water containing approximately 0.5 milligram per milliliter BMP. After 5 minutes equilibration in the cold, sufficient concentrated cold HBSS is added to restore isotonicity. This suspension is warmed to 37° C. and incubated at that temperature for 45 minutes. The resealed cells are collected by centrifugation at 1000 gs for 15 minutes and washed three times with isotonic HBSS to remove any untrapped enyzme.

The encapsulated BMP/RBC conjugate may be pelleted and the pellet placed directly into an osseous defect. The conjugate RBCs may be surface activated and partially crosslinked and incorporated into an osteogenic and/or stress-bearing implant. Monoclonal antibodies, to bone tissue antigenic markers, may be attached to the surface of the cells so that the osteogenic proteins can be directed, parenterally, to an osseous defect to promote heating.

EXAMPLE THIRTY

The method of Example Twenty such that a calcium binding protein or peptide is used to create a bond between the inorganic particle and the matrix. A calcium binding peptide of molecular weight of 5,000 to 7,000, namely, osteocalcin, which binds to hydroxyapatite may be used as the calcium binding interface in this method. The particle is immersed in a 1 to 1000 ppm solution of osteocalcin prior to drying to affect this bound. The procedure in Example Twenty is then followed.

What is claimed is:

1. A method of making a biocompatible, delivery system, comprising:
   a) dispersing a bioactive protein, peptide or drug within a plurality of protein particles selected from the group consisting of demineralized bone matrix, demineralized bone matrix extracted in chaotropic agents, reconstituted collagen or mixtures thereof;
   b) dispersing the particles of step (a) in an aqueous solution of about 0.002 to about 0.25 weight percent of a crosslinking agent and surface activating or partially crosslinking said particles;
   c) removing the particles of step (b) from the aqueous dispersion; and
   d) adding an organic matrix to said particles of step (c).

2. A method of making a biocompatible, delivery system, comprising:
   a) dispersing a bioactive protein, peptide or drug within a plurality of protein particles selected from the group consisting of demineralized bone matrix, demineralized bone matrix extracted in chaotropic agents, reconstituted collagen or mixtures thereof;

b) dispersing the particles of step (a) in an aqueous solution of about 0.002 to about 0.25 weight percent of a glutaraldehyde and surface activating or partially cross linking said particles;

c) removing the particles of step (b) from the aqueous dispersion; and d) adding an organic matrix to said particles of step (c).

3. The method of claim 1 or claim 2 wherein the organic matrix is collagen, gelatin, blood proteins, blood serum, blood plasma, fibrin, or mixtures thereof.

4. The method of claim 1 or claim 2 wherein said drug is an antibiotic.

5. The method of claim 1 or claim 2 wherein the bioactive protein or peptide is bone morphogenic protein, insulin-like growth factor, nerve growth factor, human growth hormone, bovine growth hormone, or porcine growth hormone.

6. The method of claim 1 or claim 2 wherein said particles of step (b) are each about 65% to about 70% uncrosslinked.

7. A method of making a biocompatible delivery system comprising:

b) dispersing a bioactive protein, peptide or drug within a plurality of coated inorganic particles, said inorganic particles having a protein based surface layer bound thereto;

b) dispersing the particles of step (a) in an aqueous solution of about 0.002 to about 0.25 weight percent of a glutaraldehyde and surface activating or partially cross linking said particles; and c) removing the particles of step (b) from the aqueous dispersion.

8. The method of claim 7 wherein the glutaraldehyde is in the range of about 0.002 to about 0.09 weight percent.

9. The method of claim 7 further comprising the step of treating said particles of step (a) with carbodiimide and with an amine or diamine.

10. The method of claim 9, wherein the coated inorganic particles are selected from the group consisting of calcium hydroxide, calcium phosphate, hydroxyapatite, tricalcium phosphate, or a phosphate ceramic material.

11. The method of claim 9, wherein the coated inorganic particles are prepared by coating inorganic particles with collagen, gelatin, L-Y-carboxyglutamic acid, the sodium salt of poly-L-glutamic or the random copolymer of L-glutamic acid containing at least one lysine in its repeating structure.

* * * * *